(12) United States Patent
Chao

(10) Patent No.: US 9,839,658 B2
(45) Date of Patent: Dec. 12, 2017

(54) USE OF CHI-JU-DI-HUANG-WAN IN TREATING RETINAL ISCHEMIA OR A DISEASE, CONDITION, OR DISORDER ASSOCIATED WITH RETINAL ISCHEMIA

(71) Applicants: Hsiao-Ming Chao, Taipei (TW); Chih-Chiang Hsieh, Taipei (TW)

(72) Inventor: Hsiao-Ming Chao, Taipei (TW)

(73) Assignee: Fang-Ping Chao, Taipei (TW)

( * ) Notice: Subject to any disclaimer, the term of this patent is extended or adjusted under 35 U.S.C. 154(b) by 0 days.

(21) Appl. No.: 14/953,026

(22) Filed: Nov. 27, 2015

(65) Prior Publication Data
US 2017/0151295 A1  Jun. 1, 2017

(51) Int. Cl.
| | |
|---|---|
| *A61K 36/076* | (2006.01) |
| *A61K 9/00* | (2006.01) |
| *A61K 35/644* | (2015.01) |
| *A61K 36/287* | (2006.01) |
| *A61K 36/40* | (2006.01) |
| *A61K 36/64* | (2006.01) |
| *A61K 36/65* | (2006.01) |
| *A61K 36/815* | (2006.01) |
| *A61K 36/884* | (2006.01) |
| *A61K 36/8945* | (2006.01) |

(52) U.S. Cl.
CPC .......... *A61K 36/076* (2013.01); *A61K 9/0053* (2013.01); *A61K 35/644* (2013.01); *A61K 36/287* (2013.01); *A61K 36/40* (2013.01); *A61K 36/64* (2013.01); *A61K 36/65* (2013.01); *A61K 36/815* (2013.01); *A61K 36/884* (2013.01); *A61K 36/8945* (2013.01); *A61K 2300/00* (2013.01)

(58) Field of Classification Search
None
See application file for complete search history.

(56) References Cited

U.S. PATENT DOCUMENTS

2004/0058015 A1* 3/2004 Tao .................. A61K 36/40
424/725

OTHER PUBLICATIONS https://tcmwiki.com/wiki/rhizoma-dioscoreae—accessed Mar. 1, 2017.*
https://tcmwiki.com/wiki/radix-rehmanniae-preparata—accessed Mar. 1, 2017.*
Chao HM, Chen IL, Liu JH: S-allyl L-cysteine protects the retina against kainate excitotoxicity in the rat. Am J Chin Med. 2014, 42(3):693-708.
Peng PH, Chao HM, Juan SH, Chen CF, Liu JH, Ko ML: Pharmacological preconditioning by low dose cobalt protoporphyrin induces heme oxygenase-1 overexpression and alleviates retinal ischemia-reperfusion injury in rats. Current eye research 2011, 36:238-246.
Chang YH, Lin HJ, Li WC: Clinical evaluation of the traditional chinese prescription Chi-Ju-Di-Huang-Wan for dry eye. Phytother Res 2005, 19:349-354.
Schatz A, Arango-Gonzalez B, Fischer D, Enderle H, Bolz S, Röck T, Naycheva L, Grimm C, Messias A, Zrenner E: Transcorneal electrical stimulation shows neuroprotective effects in retinas of light-exposed rats. Invest Ophthalmol Vis Sci 2012, 53:5552-5561.
Chao HM, Chuang MJ, Liu JH, Liu XQ, Ho LK, Pan WHT, Zhang XM, Liu CM, Tsai SK, Kong CW, Lee SD, Chen MM, Chao FP: Baicalein protects against retinal ischemia by antioxidation, antiapoptosis, downregulation of HIF-1alpha, VEGF, and MMP-9 and upregulation of HO-1. J Ocul Pharmacol Ther 2013, 29:539-549.
Marecko I, Cvejic D, Selemetjev S, Paskas S, Tatic S, Paunovic I, Savin S: Enhanced activation of matrix metalloproteinase-9 correlates with the degree of papillary thyroid carcinoma infiltration. Croat Med J 2014, 55:128-137.

* cited by examiner

*Primary Examiner* — Susan Hoffman
(74) *Attorney, Agent, or Firm* — Hannah M. Tien

(57) ABSTRACT

The present invention relates to a method for treating retinal ischemia, or a disease, condition, or disorder associated with retinal ischemia, in a subject in need thereof, comprising administering to said subject a therapeutically effective amount of a composition comprising Chi-Ju-Di-Huang-Wan, wherein the Chi-Ju-Di-Huang-Wan consists of Rehmanniae Radix Preparata, Corni Fructus, Rhizoma *Dioscoreae*, Poria, Cortex Moutan Radicis, Alismatis Rhizome, Fructus Lycii, and *Chrysanthemi* Flos.

8 Claims, 12 Drawing Sheets
(6 of 12 Drawing Sheet(s) Filed in Color)

Fig. 2A  Fig. 2B  Fig. 2C  Fig. 2D
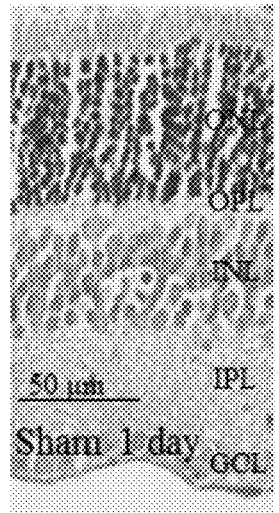 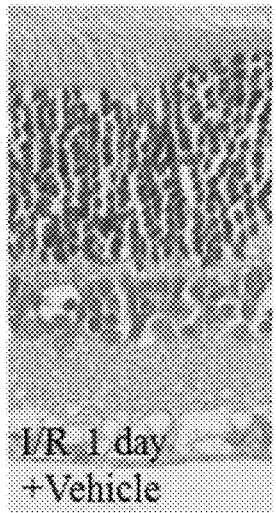 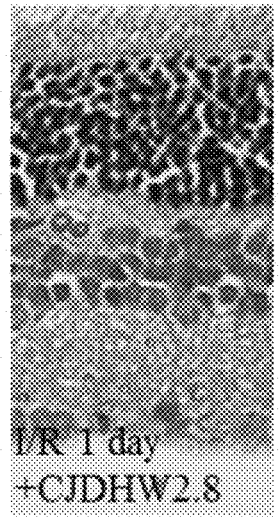 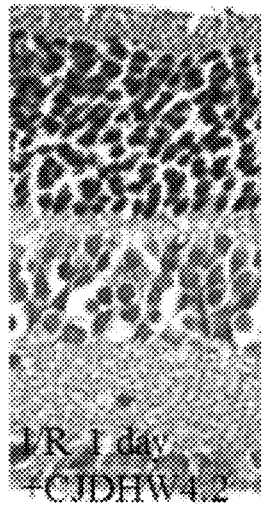
Fig. 2E
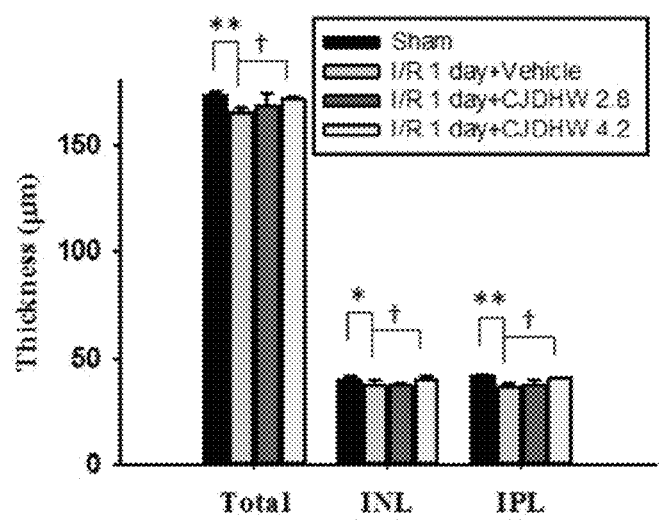

Fig. 2F  Fig. 2G  Fig. 2H  Fig. 2I
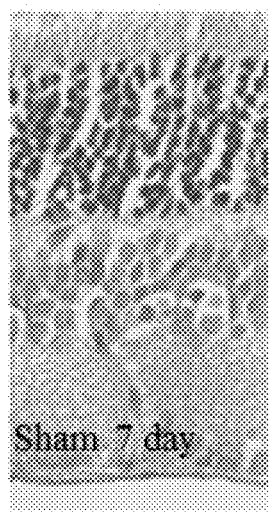  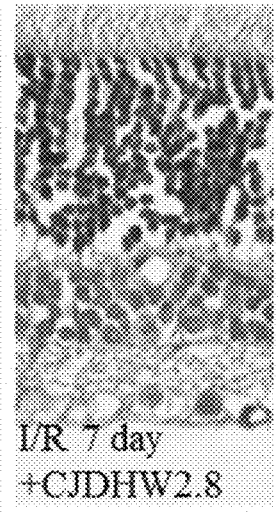 
Fig. 2J
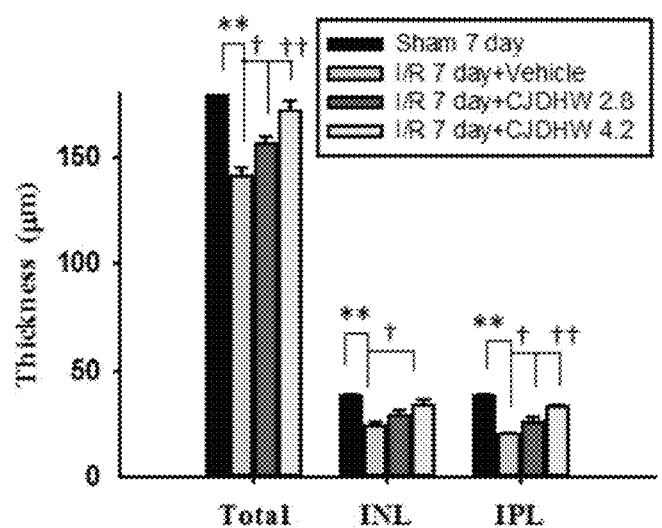

Fig. 3F  Fig. 3G  Fig. 3H  Fig. 3I
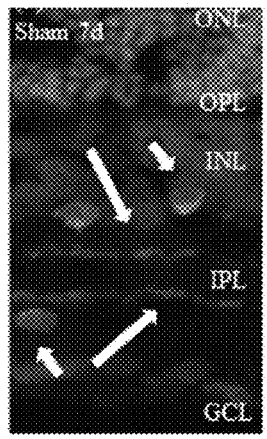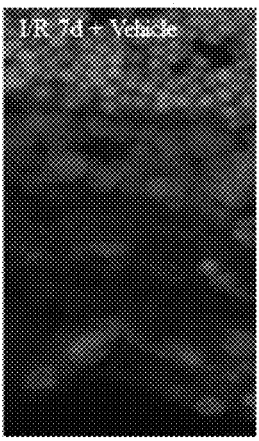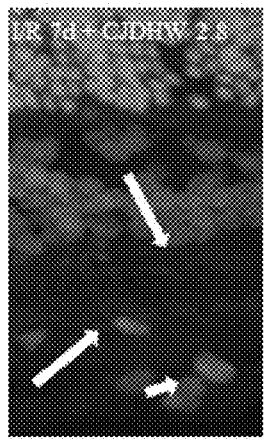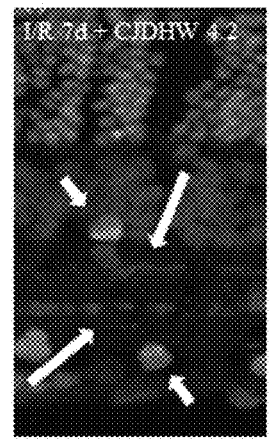
Fig. 3J
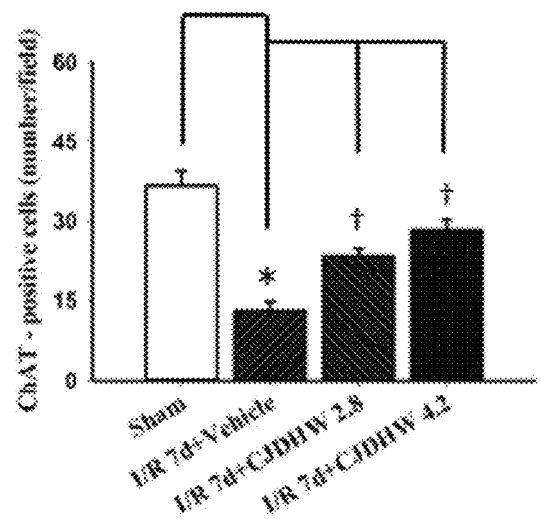

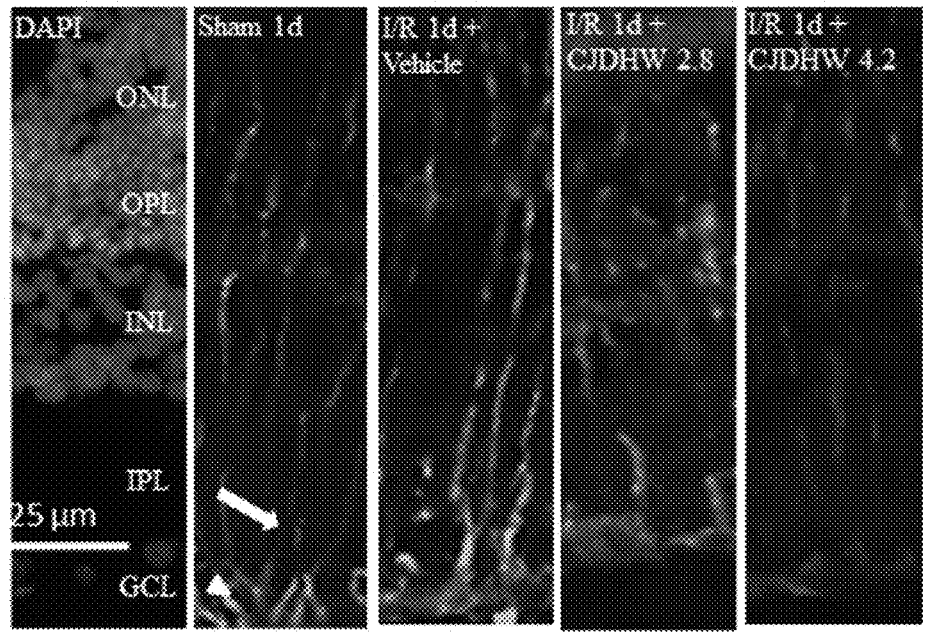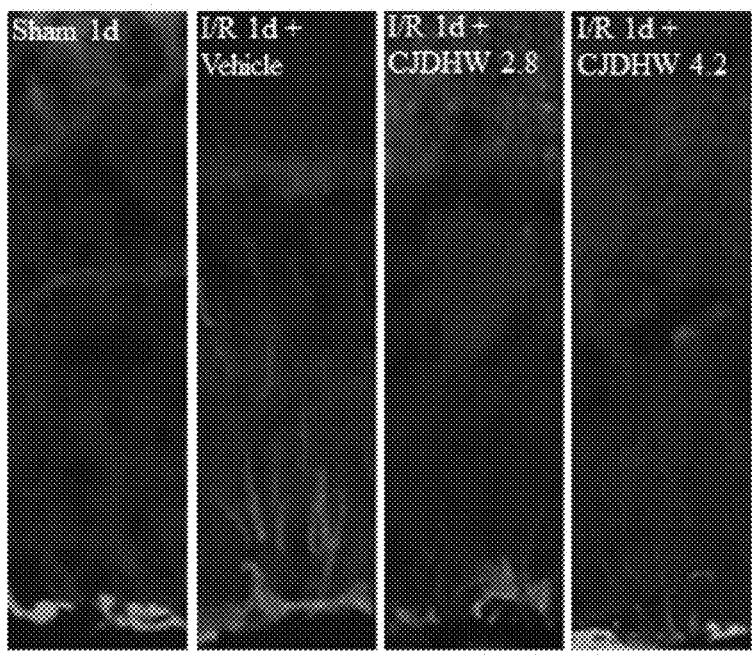

Fig. 4J  Fig. 4K  Fig. 4L  Fig. 4M  Fig. 4N
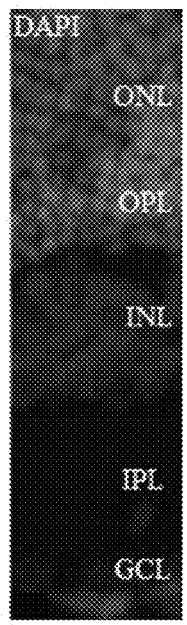 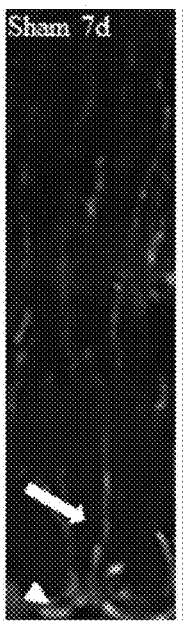 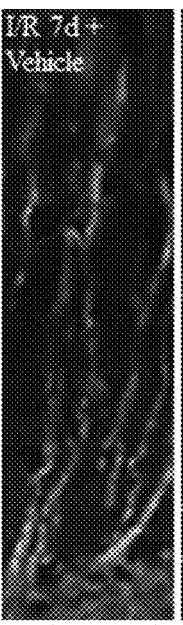 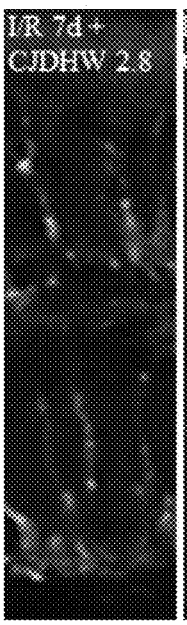 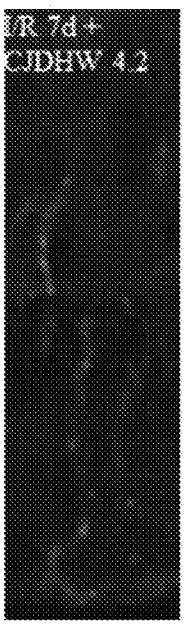
Fig. 4O  Fig. 4P  Fig. 4Q  Fig. 4R
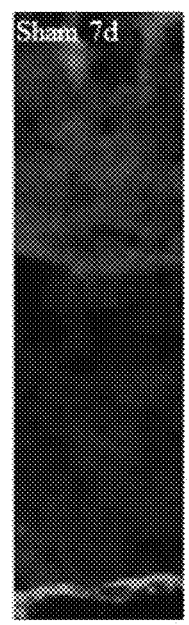 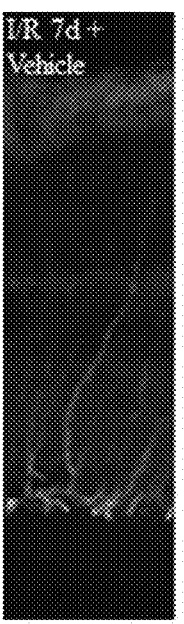 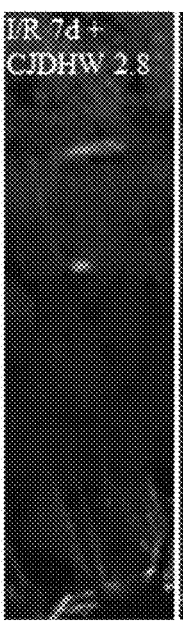 

Fig. 5A   Fig. 5B   Fig. 5C   Fig. 5D
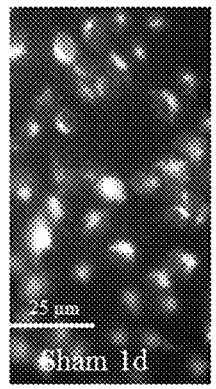 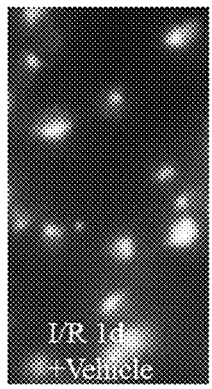 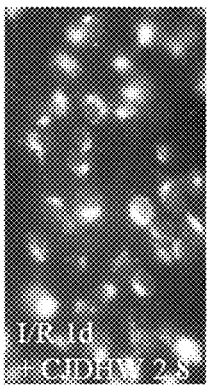 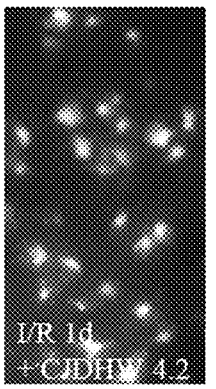
Fig. 5E
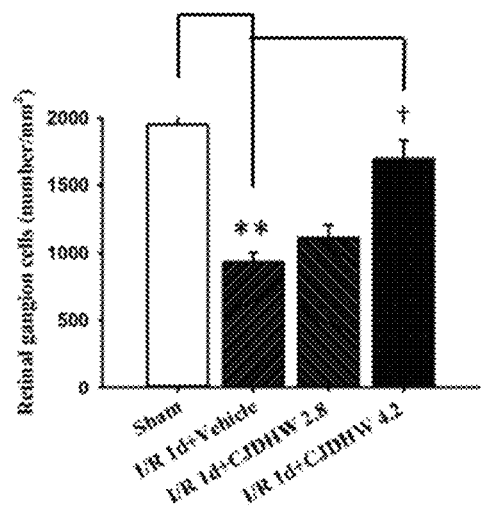

Fig. 8
(A)
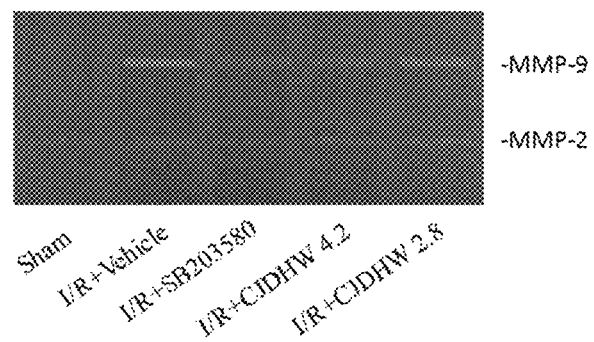
(B)
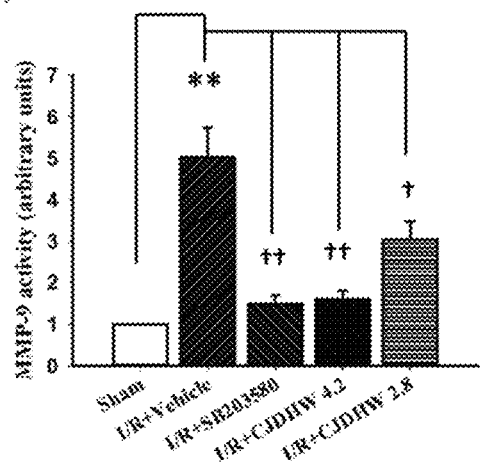

```
                              SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Forward primer for beta-Actin.
<220> FEATURE:
<221> NAME/KEY: primer_bind
<222> LOCATION: (1)..(20)

<400> SEQUENCE: 1
agggaaatcg tgcgtgacat                                                       20

<210> SEQ ID NO 2
<211> LENGTH: 20
<212> TYPE: DNA
<213> ORGANISM: Artificial Sequence
<220> FEATURE:
<223> OTHER INFORMATION: Reverse primer for beta-Actin.
<220> FEATURE:
<221> NAME/KEY: primer_bind
<222> LOCATION: (1)..(20)

<400> SEQUENCE: 2
gaaccgctca ttgccgatag                                                       20

<210> SEQ ID NO 3
<211> LENGTH: 20
<212> TYPE: DNA
<213> ORGANISM: Artificial Sequence
<220> FEATURE:
<223> OTHER INFORMATION: Forward primer for Thy-1.
<220> FEATURE:
<221> NAME/KEY: primer_bind
<222> LOCATION: (1)..(20)

<400> SEQUENCE: 3
accaaggatg agggcgacta                                                       20

<210> SEQ ID NO 4
<211> LENGTH: 21
<212> TYPE: DNA
<213> ORGANISM: Artificial Sequence
<220> FEATURE:
<223> OTHER INFORMATION: Reverse primer for Thy-1.
<220> FEATURE:
<221> NAME/KEY: primer_bind
<222> LOCATION: (1)..(21)

<400> SEQUENCE: 4
caggcttatg ccaccacact t                                                     21

<210> SEQ ID NO 5
<211> LENGTH: 20
<212> TYPE: DNA
<213> ORGANISM: Artificial Sequence
<220> FEATURE:
<223> OTHER INFORMATION: Forward primer for MMP-9.
<220> FEATURE:
<221> NAME/KEY: primer_bind
<222> LOCATION: (1)..(20)
```

```
<400> SEQUENCE: 5
tgcgctgggc ttagatcatt                                            20

<210> SEQ ID NO 6
<211> LENGTH: 23
<212> TYPE: DNA
<213> ORGANISM: Artificial Sequence
<220> FEATURE:
<223> OTHER INFORMATION: Reverse primer for MMP-9.
<220> FEATURE:
<221> NAME/KEY: primer_bind
<222> LOCATION: (1)..(23)

<400> SEQUENCE: 6
tggatgcctt ttatgtcgtc ttc                                        23
```

USE OF CHI-JU-DI-HUANG-WAN IN TREATING RETINAL ISCHEMIA OR A DISEASE, CONDITION, OR DISORDER ASSOCIATED WITH RETINAL ISCHEMIA

FIELD OF THE INVENTION

The present invention relates to use of Chi-Ju-Di-Huang-Wan (a traditional Chinese medicine prescription consisting of Rehmanniae Radix Preparata, Corni Fructus, Rhizoma *Dioscoreae*, Poria, Cortex Moutan Radicis, Alismatis Rhizome, Fructus Lycii, and *Chrysanthemi* Flos) in the treatment of retinal ischemia. The invention relates more particularly to the use of a composition comprising Chi-Ju-Di-Huang-Wan intended for the treatment and/or the prevention of a retinal ischemia and disease, condition, or disorder associated with retinal ischemia.

BACKGROUND OF THE INVENTION

Retinal vascular occlusion, glaucoma, diabetic retinopathy and age related macular degeneration (AMD) are related to retinal ischemia. Retinal vascular occlusion includes such as central or branch retinal artery occlusion (CRAO or BRAO). The defined ocular disorders often result in serious complications. Thus, the treatment of retinal ischemic injury is vital.

Amacrines and their neuronal processes are susceptible to ischemia plus reperfusion (I/R). After I/R, the immunolabelings of vimentin/glial fibrillary acidic protein (GFAP) are enhanced in Müllers. Matrix metalloproteinase-9 (MMP-9) is proteolytic and able to degrade the extracellular matrix. Ischemia has been also shown to lead to the retinal ganglion cell (RGC) death that is associated with increased MMP-9 levels. On the other hand, HO-1 is an inducible isoform that is involved in the response to oxidative stress and hypoxia. Increased levels of HO-1 would seem to be able to provide a protective effect against retinal ischemia and/or AMD via antioxidative activity.

Mitogen-activated protein kinases (MAPKs) are key kinases in signal transduction pathways. Moreover, major members of MAPK subfamily (JNK, p38, and ERK1/2) have been implicated in neuronal injury and diseases. The MAPK protein, p38, which is stimulated by various stresses including ischemia and oxidative stress, has been shown to be involved in apoptosis.

"Chi-Ju-Di-Huang-Wan" (CJDHW; Sun Ten Pharmaceutical Co., Taipei, Taiwan) is a traditional Chinese herbal recipe which consists of the formula "Liu Wei Di Huang Wan" (Rehmanniae Radix Preparata, Corni Fructus, Rhizoma *Dioscoreae*, Poria, Cortex Moutan Radicis, Alismatis Rhizome) plus Fructus Lycii and *Chrysanthemi* Flos. Sometimes honey will be additionally added into the recipe in order to enhance flavor and make the elderly and children easy to swallow (Chang Y H, Lin H J, Li W C: Clinical evaluation of the traditional chinese prescription Chi-Ju-Di-Huang-Wan for dry eye. *Phytother Res* 2005, 19:349-354). "CJDHW" has been reported to be an effective treatment in dry eye. "CJDHW" is an effective stabilizer of the tear film and decreases abnormalities of the corneal epithelium. However, the therapeutic mechanism(s) associated with of the effects of CJDHW remain unknown. Active known compounds in this formula include the antioxidant zeaxanthin and lutein, which are present in Fructus Lycii and *Chrysanthemi* Flos, as well as trehalose, which is present in Rehmanniae Radix Preparata.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A: When compared to the sham procedure retina as a control, there was a considerable reduction in the amplitudes ERG b-wave following pressure-induced retinal ischemia and preadministration of vehicle in a representative animal of the I/R+Vehicle group. Dose-responsive counteraction of this reduction was shown with preadministration of CJDHW (at 2.8 g/kg/day, I/R+CJDHW2.8; at 4.2 g/kg/day, I/R+CJDHW4.2) in one rat from each defined group. FIG. 1B: In contrast with the control sham group, there was a significant (*; $p<0.05$) decrease in the b-wave ratio in the I/R+Vehicle group at 1, 3, 5 and 7 days following ischemia. Dose-responsive and significant (†; $p<0.05$) attenuation of this ischemia-induced decrease was achieved with preadministration of 2.8 g/Kg/day (I/R+CJDHW2.8) and 4.2 g/Kg/day of CJDHW (I/R+CJDHW4.2). The results are expressed as mean±SEM (n=5). CJDHW, Chi-Ju-Di-Huang-Wan.

FIGS. 2A-2J: The thickness of various retinal layers. These figures show sections of retina from approximately the same eccentricity. FIG. 2A or FIG. 2F is from a control retina 1 day (Sham 1 d) or 7 days following the sham procedure (Sham 7 d), respectively. FIG. 2B or FIG. 2G is respectively from a retina that received ischemia plus reperfusion of 1 day (I/R 1 d+Vehicle) or 7 days and pretreatment of vehicle (I/R 7 d+Vehicle). As compared to the control retina (FIG. 2A; FIG. 2F), the thickness of the inner retina (INL, IPL and GCL) in the ischemic retina pretreated with vehicle (FIG. 2B; FIG. 2G) appears considerably reduced. This reduction of the inner retinal layers is attenuated in animals given ischemia plus reperfusion of 1 or 7 days and pretreated with 2.8 g/Kg/day (FIG. 2C, I/R 1 d+CJDHW2.8; FIG. 2H, I/R 7 d+CJDHW2.8) and 4.2 g/Kg/day of CJDHW (FIG. 2D, I/R 1 d+CJDHW4.2; FIG. 2I, I/R 7 d+CJDHW4.2). Scale bar=50 µm. Morphometric analysis of the thickness of the various retinal layers from sections of similar eccentricity is shown (FIG. 2E; FIG. 2J). As compared to the control retina (Sham 1 d; Sham 7 d), the thickness of the whole retinal layer, the inner nuclear layer (INL) and the inner plexiform layer (IPL) was significantly reduced in the vehicle-treated ischemic retinas. Moreover, this reduction was dose-dependently and significantly attenuated when ischemic retinas were pretreated with 2.8 and 4.2 g/Kg/day of CJDHW. Results are mean±S.E.M. of the number of experiments (n=4~6). * Significantly different ($p<0.05$) from the control eyes. † Significantly different ($p<0.05$) from the I/R 1 d+Vehicle or I/R 7 d+Vehicle group. Total: whole retina.

FIGS. 3A-3J: Choline acetyltransferase (ChAT; red) immunohistochemistry. In the sham procedure retina at 1 day (FIG. 3A; Sham 1 d) and at 7 days (FIG. 3F; Sham 7 d), amacrine cell bodies (short arrows) were located in the inner nuclear layer (INL) and ganglion cell layer (GCL); the neuronal processes displayed two well-delineated bands (long arrows) in the inner plexiform layer (IPL). Retinal ischemia plus 1 or 7 days of reperfusion caused a considerable reduction the IPL's ChAT immunolabeling as well as the ChAT immunolabeled amacrine cell body number was less numerous; the preadministered vehicle didn't influence the defined ischemic changes (FIG. 3B, I/R 1 d+Vehicle; FIG. 3G, I/R 7 d+Vehicle). Nonetheless, the ischemic alterations were clearly alleviated with preadministration of 2.8 g/Kg/day (FIG. 3C, I/R 1 d+CJDHW2.8; FIG. 3H, I/R 7 d+CJDHW2.8) and 4.2 g/Kg/day of CJDHW (FIG. 3D, I/R 1 d+CJDHW4.2; FIG. 3I, I/R 7 d+CJDHW4.2). The ChAT immunolabeled images were merged with those of 4,6-diamidine-2-phenylindole dihydrochloride (DAPI, blue; FIGS. 3A-3D; FIGS. 3F-3I). Each bar represents the mean±SEM (n=6) at 1 day (FIG. 3E) and 7 days following the sham procedure or ischemia (FIG. 3J). * represents significance ($p<0.05$; sham vs. I/R 1 d+Vehicle; sham vs. I/R 7 d+Vehicle). † represents significance ($p<0.05$; I/R 1 d+Vehicle vs. I/R 1 d+CJDHW2.8 or I/R 1 d+CJDHW4.2; I/R 7 d+Vehicle vs. I/R 7 d+CJDHW2.8 or I/R 7 d+CJDHW4.2). CJDHW, Chi-Ju-Di-Huang-Wan. Scale bar=35 µm.

FIGS. 4A-4R: Vimentin immunohistochemistry. At 1 (FIG. 4B, Sham 1 d) or 7 days day following the sham procedure (FIG. 4K, Sham 7 d), the Müller cells were demonstrated with vimentin (green) immunolabeling at the end feet (arrow heads) in the ganglion cell layer (GCL) and at the processes in the inner plexiform layer (IPL; arrows), inner nuclear layer (INL) and outer nuclear layer (ONL). In contrast with the sham retina, anti-vimentin immunolabeling was increased one or seven days after ischemia with preadministration of vehicle (FIG. 4C, I/R 1 d+Vehicle; FIG. 4L, I/R 7 d+Vehicle). This enhancement was attenuated by pretreatment with 2.8 g/Kg/day (FIG. 4D, I/R 1 d+CJDHW2.8; FIG. 4M, I/R 7 d+CJDHW2.8) or 4.2 g/Kg/day of CJDHW (FIG. 4E, I/R 1 d+CJDHW4.2; FIG. 4N, I/R 7 d+CJDHW4.2). The cellular nuclei of the sham retina (FIG. 4A; FIG. 4J) were immunolabeled with 4,6-diamidine-2-phenylindole dihydrochloride (DAPI; blue). GFAP immunohistochemistry. In contrast with the control retina one (FIG. 4F; Sham 1 d) or seven days following the sham procedure (FIG. 4O; Sham 7 d), anti-GFAP immunolabeling was also increased 1 or 7 days day after ischemia with preadministered vehicle (FIG. 4G, I/R 1 d+Vehicle; FIG. 4P, I/R 7 d+Vehicle). This enhancement was blunted by pretreatment with 2.8 g/Kg/day (FIG. 4H, I/R 1 d+CJDHW2.8; FIG. 4Q, I/R 7 d+CJDHW2.8) or 4.2 g/Kg/day of CJDHW (FIG. 4I, I/R 1 d+CJDHW4.2; FIG. 4R, I/R 7 d+CJDHW4.2). GFAP, glial fibrillary acidic protein; CJDHW, Chi-Ju-Di-Huang-Wan. Scale bar=25 µm.

FIGS. 5A-5J: Fluorogold-labeling. The microscopic images show the density of retinal ganglion cells (RGCs) at 1 and 7 days after the sham-procedure (FIG. 5A, Sham 1 d; FIG. 5F, Sham 7 d), or at 1 and 7 days of reperfusion following ischemia with preadministered vehicle (FIG. 5B, I/R 1 d+Vehicle; FIG. 5G, I/R 7 d+Vehicle) or Chi-Ju-Di-Huang-Wan at 2.8 g/Kg/day (FIG. 5C, I/R 1 d+CJDHW2.8; FIG. 5H, I/R 7 d+CJDHW2.8) and at 4.2 g/kg/day (FIG. 5D, I/R 1 d+CJDHW4.2; FIG. 5I, I/R 7 d+CJDHW4.2). Each bar indicates the mean±SEM (FIG. 5E; FIG. 5J; n=3). ** indicates significant difference ($p<0.01$; sham vs. I/R 1 d+Vehicle or I/R 7 d+Vehicle); † indicates significant difference ($p<0.05$; I/R 1 d+Vehicle vs. I/R 1 d+CJDHW4.2; I/R 7 d+Vehicle vs. I/R 7 d+CJDHW4.2). Scale bars=25 µm.

FIG. 8: Gel zymography. (A) An example of a gelatin zymogram used for the quantification of matrix metalloproteinase-9 (MMP-9) quantitation protein expression by densitometry. Gelatinolytic bands of 72 and 97 kDa corresponded to MMP-2 and active MMP-9, respectively. Lane 1, the sham procedure retina (Sham); Lane 2, the vehicle-pretreated ischemic retina (I/R+Vehicle); Lane 3, the SB203580 (p38 MAPK inhibitor)-pretreated ischemic retina (I/R+SB203580); Lanes 4 and 5, the ischemic retina respectively pretreated with 4.2 g/kg/day (I/R+CJDHW4.2) and 2.8 g/kg/day of CJDHW (I/R+CJDHW2.8). (B) Each bar indicates the mean±SEM (n=4~5). ** indicates significance ($p<0.01$; sham vs. I/R+Vehicle). †† indicates significance ($p<0.01$; I/R+Vehicle vs. I/R+CJDHW4.2; I/R+Vehicle vs. SB203580). † indicates significance ($p<0.05$; I/R+Vehicle vs. I/R+CJDHW2.8). In contrast to the results for MMP-9, the expression of MMP-2, when measured at 24 hours after ischemia and pretreatment with vehicle or CJDHW4.2/CJDHW2.8, was found to have a similar protein expression level to that of the control group (Sham).

SUMMARY OF THE INVENTION

Figure 1A:
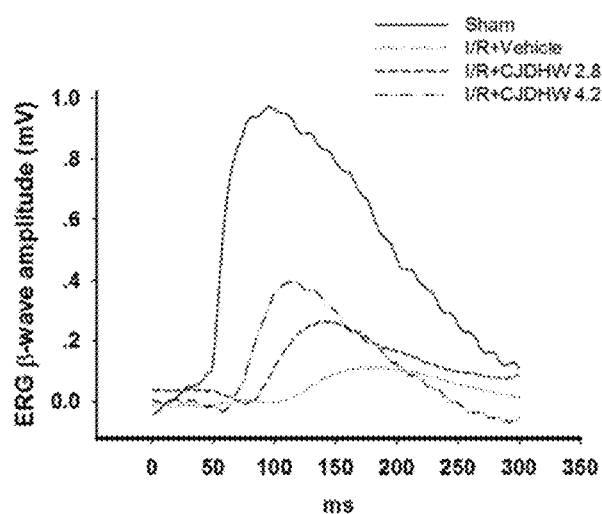
FIGS. 1A-1B: Electroretinogram (ERG): The effect of CJDHW on retinal ischemia plus reperfusion (I/R).

The present invention relates to a method for treating retinal ischemia, or a disease, condition, or disorder associated with retinal ischemia, in a subject in need thereof, comprising administering to said subject a therapeutically effective amount of a composition comprising Chi-Ju-Di-Huang-Wan, wherein the Chi-Ju-Di-Huang-Wan consists of Rehmanniae Radix Preparata, Corni Fructus, Rhizoma *Dioscoreae*, Poria, Cortex Moutan Radicis, Alismatis Rhizome, Fructus Lycii, and *Chrysanthemi* Flos.

DETAILED DESCRIPTION OF THE INVENTION

This study examines whether Chi-Ju-Di-Huang-Wan (CJDHW) is able to attenuate retinal ischemic injury and its effects are assessed by electrophysiology, retinal thickness, choline acetyltransferase (ChAT) immunochemistry, vimentin/glial fibrillary acidic protein (GFAP) immunochemistry (indexing Müller cells), fluorogold retrograde RGC labeling, TUNEL staining (for apoptotic cells), Bcl-2/HO-1/phosphorylated-p38 (P-p38)/MMP-9 protein level analysis and MMP-9 activity as measured by zymography, as well as by measurement of the mRNA expression levels of Thy-1 and MMP-9.

The defined retinal ischemic alterations include the following features, a reduction in ERG b-wave amplitudes, a decrease in inner retinal thickness, a decrease in choline acetyltransferase (ChAT) immunolabeling, enhanced vimentin/glial fibrillary acidic protein (GFAP) immunoreactivity, more numerous apoptotic cells in the ganglion cell layer, and less numerous retinal ganglion cells. Moreover, a decrease and an increase in the mRNA levels of Thy-1 and matrix metalloproteinase-9 (MMP-9) are found in the ischemic retina, respectively. Furthermore, the protein level of B-cell lymphoma 2 (Bcl-2) is decreased while the levels of heme oxygenase-1 (HO-1), phosphorylated-p38 (P-p38), mitogen-activated protein kinase (MAPK) and MMP-9 increased. Importantly, the ischemia-induced changes are significantly modulated by pretreatment of 4.2 g/Kg/day CJDHW. In particular, the ischemia-associated P-p38 and MMP-9 increases are blunted by both CJDHW and 2 nmole of SB203580, a p38 MAPK inhibitor.

The present invention demonstrates various ischemic alterations in the rat retina by electroretinography (b-wave indexing Müller and bipolar cells), immunohistochemistry (ChAT labeling amacrine cells, vimentin/GFAP labeling Müller cells, fluorogold labelling RGCs), histopathology (retinal thickness measurement, TUNEL-positive cells in the RGC layer), Western blotting (Bcl-2, HO-1, P-p38 and MMP-9), and real-time PCR analysis (Thy-1 and HO-1). Importantly, all these defined ischemia-related characteristic features are significantly modulated by CJDHW treatment before I/R. CJDHW protects against retinal ischemic injury by preserving the retinal electrophysiological function (FIGS. 1A-1B), by counteracting the inner retina thickness reduction or cholinergic neuron death (FIGS. 2A-2J and 3A-3J; Tables 2 and 3), by attenuating Müller cell vimentin/GFAP glial activation (FIGS. 4A-4R), by decreasing the number of apoptotic cells in the RGC layer (Table 4) as well as by blunting the Thy-1 mRNA downregulation (FIG. 6 and Table 6) and by reducing RGC death as detected by fluorogold labeling (FIGS. 5A-5J; Table 5). As shown by the present Western blot assay results (FIG. 7 and Table 7), CJDHW is able to protect the ischemia-injured retinal cells such as amacrine cells and RGCs (FIGS. 3A-3J, 5A-5J and 6; Tables 3, 5 and 6); it seems likely that this, at least in part, is associated with the antioxidative effect due to HO-1 overexpression (FIG. 7 and Table 7). Most importantly, the increased level and enhanced activity of MMP-9 are inhibited by both CJDHW and the p38 MAPK inhibitor, SB203580 (FIGS. 7 and 8). In such circumstances, it is a reasonable conclusion that CJDHW is able to bring about neuroprotection with respect to retinal ischemia through an antioxidative effect and via an antiapoptotic effect (increased levels HO-1 and Bcl-2, respectively). Above all, CJDHW also appears to protect against retinal ischemia by down-regulating MMP-9 via p38 MAPK inhibition. In the present invention, it is shown that preadministration of CJDHW is clinically important as a preventive approach when patients have a family history of AMD or diabetes, and/or when there are predisposing factors related to CRAO or BRAO, namely hypertension, coronary/carotid artery disease, hyperlipidemia or heart valve disorder. The electrophysiologic results of the present invention indicate that the post-ischemic administration of CJDHW significantly attenuates retinal ischemia-associated visual dysfunction (b-wave reduction). Consequently, CJDHW is useful in preventing or mitigating neuronal damage in both acute and possibly early chronic retinal ischemic injury. Therefore, CJDHW can be a useful approach to protecting against defined vision-threatening retinal ischemic disorders, such as central retinal artery occlusion, central retinal vein occlusion, other retinal vascular occlusive disorders, glaucomatous optic neuropathy, diabetic retinopathy and wAMD.

Therefore, the present invention provides a method for treating retinal ischemia, or a disease, condition, or disorder associated with retinal ischemia, in a subject in need thereof, comprising administering to said subject a therapeutically effective amount of a composition comprising Chi-Ju-Di-Huang-Wan, wherein the Chi-Ju-Di-Huang-Wan consists of Rehmanniae Radix Preparata, Corni Fructus, Rhizoma *Dioscoreae*, Poria, Cortex Moutan Radicis, Alismatis Rhizome, Fructus Lycii, and *Chrysanthemi* Flos. In an embodiment, the composition further comprises honey. In an embodiment, the disease, condition, or disorder associated with retinal ischemia comprises retinal vascular occlusion, glaucoma, diabetic retinopathy, or age related macular degeneration. Because retina is the extension of the central nervous system, one skilled in the art can reasonably make an inference that this method can be further used for treating brain ischemia (stroke). Preferably, the subject is a mammal. More preferably, the subject is human. Preferably, the composition is administered orally.

In an embodiment, the therapeutically effective amount of the composition comprises a dose of Chi-Ju-Di-Huang-Wan ranges from about 1 g/kg/day to about 10 g/kg/day. In another embodiment, the therapeutically effective amount of the composition comprises a dose of Chi-Ju-Di-Huang-Wan ranges from about 1 g/kg/day to about 5 g/kg/day. In yet another embodiment, the therapeutically effective amount of the composition comprises a dose of Chi-Ju-Di-Huang-Wan ranges from about 2.8 g/kg/day to about 4.2 g/kg/day. In yet another embodiment, the therapeutically effective amount of the composition comprises a dose of Chi-Ju-Di-Huang-Wan ranges from about 2.8 g/kg/day to about 4.2 g/kg/day for orally administration in rodent.

It is noted that the dosage described above is mainly for using in rats by orally administration. Therefore, if the subject in need of such treatment is a human, then the dosage should be recalculated according to known conversion methods in the art. For example, the conversion of the dosage between a rat (with a standard body weight of 0.2 kg) and a human (with a standard body weight of 70 kg) can be as follows:

$$1 \text{ (g/kg)} \times 0.2 \times 56/70 = 0.16 \text{ (g/kg)};$$

$$2.8 \text{ (g/kg)} \times 0.2 \times 56/70 = 0.448 \text{ (g/kg)};$$

$$4.2 \text{ (g/kg)} \times 0.2 \times 56/70 = 0.672 \text{ (g/kg)};$$

$$5 \text{ (g/kg)} \times 0.2 \times 56/70 = 0.8 \text{ (g/kg)}; \text{ or}$$

$$10 \text{ (g/kg)} \times 0.2 \times 56/70 = 1.6 \text{ (g/kg)}.$$

That is, the dose of 1-10 g/kg for using in rats is approximately equal to 0.16-1.6 g/kg for using in humans.

Therefore, in an embodiment, the dose of Chi-Ju-Di-Huang-Wan for human can range from about 0.1 g/kg/day to about 2 g/kg/day, from about 0.16 g/kg/day to about 1.6 g/kg/day, from about 0.16 g/kg/day to about 0.8 g/kg/day, from about 0.4 g/kg/day to about 0.7 g/kg/day, or from about 0.448 g/kg/day to about 0.672 g/kg/day.

Abbreviations wAMD: wet age related macular degeneration; Bcl-2: B-cell lymphoma 2; ChAT: Choline acetyltransferase; CJDHW: Chi-Ju-Di-Huang-Wan; DAPI: 4',6-diamidino-2-phenylindole; DMSO: Dimethyl sulfoxide; ERG: Electroretinogram; GCL: Ganglion cell layer; GFAP: Glial fibrillary acidic protein; HE: Hematoxylin-eosin; HIOP: High intraocular pressure; HO-1: Heme oxygenase-1; HRP: horseradish peroxidase; Ischemia/reperfusion; P-p38: phosphorylated-p38; MAPK: Mitogen-activated protein kinases; MMP-9: Matrix metallopeptidase-9; PCR: polymerase chain reaction; RGC: retinal ganglion cell; RPE: Retinal pigment epithelium; SDS-PAGE: Sodium dodecyl sulfate polyacrylamide gel electrophoresis; TBS: Tris-buffered saline; TUNEL: Terminal deoxynucleotidyl-transferase (TdT)-mediated dUTP nick end-labeling; VEGF: Vascular endothelial growth factor.

EXAMPLES

The examples below are non-limiting and are merely representative of various aspects and features of the present invention.

Example 1

Methods
Animals

The Institutional Animal Care and Use Committee at Cheng Hsin General Hospital (CHGH; Taipei, Taiwan; Approval No: CHIACUC 102-08) agreed all the animal experiments, which complied with the Association for Research in Vision and Ophthalmology Statement for the Use of Animals in Ophthalmology and Vision Research. Wistar rats (BioLasco, Taipei, Taiwan) were raised with the 40%-60% humidity and at 19-23° C. They were maintained on a 12-h light/dark period with 12-15 air exchanges/hour. They were fed with food and water at liberty.

Animal Anesthesia as Well as Euthanasia

Anesthesia was carried out using ketamine (100 mg/kg) and xylazine (5 mg/kg), which were injected intraperitoneally given to the animals. Sodium pentobarbitone (>140 mg/kg) was intraperitoneally administered to sacrifice the animals utilizing a thoughtful way (Scientific Procedures Acts 1986).

Retinal Ischemia Establishment

After anesthesia, we kept the animals (200-250 g) in a stereotaxic frame. A 120 mmHg high intraocular pressure (HIOP) was induced and maintained for 60 minutes by cannulating a rat eye's anterior chamber with adapting a 30-gauge needle to a normal saline bottle, which was raised. The induction of an ischemic insult was confirmed by the detection of a pale eye fundus (Chao H M, Chen I L, Liu J H: S-allyl L-cysteine protects the retina against kainate excitotoxicity in the rat. *Am J Chin Med.* 2014, 42(3):693-708; Peng P H, Chao H M, Juan S H, Chen C F, Liu J H, Ko M L: Pharmacological preconditioning by low dose cobalt protoporphyrin induces heme oxygenase-1 overexpression and alleviates retinal ischemia-reperfusion injury in rats. *Current eye research* 2011, 36:238-246). The control rats' eyes received a sham procedure where the saline reservoir wasn't raised.

Drug Provision

A daily oral intake of water, a low intake of CJDHW (2.8 g/kg/day, CJDHW2.8) or a high intake of CJDHW (4.2 g/kg/day, CJDHW4.2) was given for 7 consecutive days before or after HIOP injury until the animals were sacrificed. The fellow normal eye acted as the control eye. The test rat whose eye was subjected to ischemia was fed with the relevant volume of CJDHW (I/R+CJDHW2.8; I/R+CJDHW4.2) or the "same" volume of vehicle (I/R+Vehicle).

Take an example, a rat that weighed 250 g was fed with a low dose of CJDHW (0.7 g/2.5 ml water/day), a high dose of CJDHW (1.05 g/3.5 ml water/day) or 3.5 ml of water.

Intravitreal injections were performed using a 30-gauge needle attached to a 25 μl syringe after pupil dilation with 1% tropicamide and 2.5% phenylephrine. In certain instances, intravitreal injections of 4 μl of 2 nmole SB203580 (Calbiochem, San Diego, Calif.) or vehicle (an equal volume of DMSO) were performed on ischemic eyes fifteen minutes before pressure-induced retinal ischemia.

Flash ERG Measurement

ERG data on all the animals pre-ischemia (day 0) was recorded followed by at 1, 3, 5, and 7 days post-ischemia and administration with the appropriate compounds. Dark adaptation for at least 8 hours, anesthesia during the ERG recordings and pupil dilation with 1% tropicamide and 2.5% phenylephrine were performed on the rats. A stimulus of 0.5 Hz was induced by placing a strobe 2 cm before the eye of each rat. Fifteen consecutive responses at 2-second intervals as well as 10 kHz were recorded; these responses were amplified and averaged as described previously (Chao H M, Chen I L, Liu J H: S-allyl L-cysteine protects the retina against kainate excitotoxicity in the rat. *Am J Chin Med.* 2014, 42(3):693-708). It had been widely accepted that the b-wave reflected the function of the bipolar cells and the inner layers of the retina. In order to make comparisons, the b-wave ratio was calculated, which was the treated ischemic retina's b-wave amplitude divided by the untreated contralateral normal retina's b-wave amplitude (Chao H M, Chen I L, Liu J H: S-allyl L-cysteine protects the retina against kainate excitotoxicity in the rat. *Am J Chin Med.* 2014, 42(3):693-708).

Hematoxylin and Eosin Staining

Following retinal ischemia plus 1 or 7 days of reperfusion, the eyeballs were marked at the 12 o'clock position of the cornea with silk suture; they were then enucleated and fixed in 4% paraformaldehyde at 4° C. for 24 h. After fixation, the anterior segment was removed, and the posterior eyeball containing the optic disc was dehydrated in a graded ethanol series and embedded in paraffin. For hematoxylin and eosin (HE) stain (Schatz A, Arango-Gonzalez B, Fischer D, Enderle H, Bolz S, Röck T, Naycheva L, Grimm C, Messias A, Zrenner E: Transcorneal electrical stimulation shows neuroprotective effects in retinas of light-exposed rats. *Invest Ophthalmol Vis Sci* 2012, 53:5552-5561), 5 μm thick sections were taken along the vertical meridian and observed under a light microscope (Leica, Heidelberg, Germany).

To quantify the retinal ischemic injury, various layer thicknesses were measured. The overall retinal thicknesses (from the inner limiting membrane to the RPE layer), the inner retinal thickness [(from the inner limiting membrane to the inner nuclear layer (INL)], and the thickness of the inner plexiform layer (IPL) were measured. All measurements were carried out approximately 1000 μm from the optic disc. Three sections per eye were averaged. Furthermore, in order to appropriately investigate any differences in the thickness between the four groups (sham, I/R+Vehicle, I/R+CJDHW2.8 and I/R+CJDHW4.2), the various thicknesses were measured by research staff blinded to the source of the tissue.

Immunofluorescence Analysis

After sacrifice, intracardial perfusion with normal saline (w/v) was given to the rats; thereafter, the retinal sections were retrieved, soaked with 4% (w/v) paraformaldehyde for 45 minutes fixation and immersed in 30% sucrose for cryosection (Chao H M, Chen I L, Liu J H: S-allyl L-cysteine protects the retina against kainate excitotoxicity in the rat. *Am J Chin Med.* 2014, 42(3):693-708). Retinal sections were collected 1 and 7 days following retinal ischemia with preadministration of CJDHW or vehicle, or following the sham procedure. Overnight, the retinal samples were incubated with primary antibodies: goat anti-ChAT polyclonal antibody, mouse anti-vimentin monoclonal antibody and rabbit anti-GFAP polyclonal antibody as described previously (Chao H M, Chen I L, Liu J H: S-allyl L-cysteine protects the retina against kainate excitotoxicity in the rat. *Am J Chin Med.* 2014, 42(3):693-708). Afterwards, we incubated the retinal samples with secondary antibody: rhodamine-conjugated rabbit anti-goat antibody, fluorescein isothiocyanate-conjugated goat anti-mouse IgG or FITC-conjugated goat anti-rabbit IgG as described previously (Chao H M, Chen I L, Liu J H: S-allyl L-cysteine protects the retina against kainate excitotoxicity in the rat. *Am J Chin Med.* 2014, 42(3):693-708). In parallel, the cellular nuclei were stained with 4,6-diamidine-2-phenylindole dihydrochloride as described previously (Chao H M, Chen I L, Liu J H: S-allyl L-cysteine protects the retina against kainate excitotoxicity in the rat. *Am J Chin Med.* 2014, 42(3):693-708). A fluorescence microscope was utilized to evaluate the retinal samples as described previously (Chao H M, Chen I L, Liu J H: S-allyl L-cysteine protects the retina against kainate excitotoxicity in the rat. *Am J Chin Med.* 2014, 42(3):693-708).

Terminal Deoxynucleotidyl-Transferase (TdT)-Mediated dUTP Nick End-Labeling (TUNEL) Assay One and seven days after I/R, the eyes were removed for TUNEL staining (In situ Cell Death Detection Kit, Fluorescein; Roche; Mannheim, Germany) to investigate cell apoptosis. The retinal samples was fixed with 10% formaldehyde for 24 h afterwards. The retinal samples were soaked with proteinase K (25 µg/ml) followed by incubation in $H_2O_2$/methanol for 5 minutes at 25° C. to inactivate endogenous peroxidases. Negative and positive controls were measured as described previously (Peng P H, Chao H M, Juan S H, Chen C F, Liu J H, Ko M L: Pharmacological preconditioning by low dose cobalt protoporphyrin induces heme oxygenase-1 overexpression and alleviates retinal ischemia-reperfusion injury in rats. *Current eye research* 2011, 36:238-246). After washing with Tris buffered saline, the retinal samples were soaked with a TdT enzyme/labeling reaction mix at 37° C. for 90 minutes. This reaction was initialized on the binding of digoxigenin-dUTP to the 3'-OH end of DNA by TdT, followed by incubation in an anti-digoxigenin antibody conjugated with peroxidase. Upon termination of the labeling reaction in stop buffer, the retinal sections were processed in a standard streptavidin-horseradish peroxidase (HRP) reaction with 3,3' diaminobenzidine as the chromogenic peroxidase substrate, and counterstained with methyl green. The average number of TUNEL positive cells per field was counted as described previously (Peng P H, Chao H M, Juan S H, Chen C F, Liu J H, Ko M L: Pharmacological preconditioning by low dose cobalt protoporphyrin induces heme oxygenase-1 overexpression and alleviates retinal ischemia-reperfusion injury in rats. *Current eye research* 2011, 36:238-246).

Retrograde Labeling of RGCs

After anesthesia, the rats were made a 2-cm incision in the scalp, and drilled two small holes into the skull as described previously (Peng P H, Chao H M, Juan S H, Chen C F, Liu J H, Ko M L: Pharmacological preconditioning by low dose cobalt protoporphyrin induces heme oxygenase-1 overexpression and alleviates retinal ischemia-reperfusion injury in rats. *Current eye research* 2011, 36:238-246). Next, 2 µl of 5% fluorogold (Sigma-Aldrich) were injected by a micropipette at depths of 3.8, 4.0, and 4.2 mm below the skull. Three days after retrograde immunolabeling of RGCs, HIOP was carried out on the right eyes of the animals whose fellow eyes served as the sham. The retina was gently retrieved, fixated, dissected and processed as described previously (Peng P H, Chao H M, Juan S H, Chen C F, Liu J H, Ko M L: Pharmacological preconditioning by low dose cobalt protoporphyrin induces heme oxygenase-1 overexpression and alleviates retinal ischemia-reperfusion injury in rats. *Current eye research* 2011, 36:238-246) The average RGC density was defined as the ratio of the total RGC number to the total retinal area evaluated (Peng P H, Chao H M, Juan S H, Chen C F, Liu J H, Ko M L: Pharmacological preconditioning by low dose cobalt protoporphyrin induces heme oxygenase-1 overexpression and alleviates retinal ischemia-reperfusion injury in rats. *Current eye research* 2011, 36:238-246).

Measurement of the Concentrations of Various Retinal mRNAs

The retinal mRNA concentrations of Thy-1 and MMP-9 were investigated utilizing a real-time polymerase chain reaction (PCR) technique (Chao H M, Chen I L, Liu J H: S-allyl L-cysteine protects the retina against kainate excitotoxicity in the rat. *Am J Chin Med.* 2014, 42(3):693-708). One day following retinal ischemia with either preadministration of mentioned compounds or following a sham procedure, the animals were sacrificed and the retinal sampled were processed as described previously (Chao H M, Chen I L, Liu J H: S-allyl L-cysteine protects the retina against kainate excitotoxicity in the rat. *Am J Chin Med.* 2014, 42(3):693-708). Retinal RNA was extracted and first strand complementary DNA (cDNA) synthesis was carried out on 2 µg deoxyribonuclease (DNase)-treated RNA. The first-strand cDNA subsequently went on real-time PCR. The PCR and cycling were performed as instructed previously (Chao H M, Chen I L, Liu J H: S-allyl L-cysteine protects the retina against kainate excitotoxicity in the rat. *Am J Chin Med.* 2014, 42(3):693-708). Relative quantitation was carried out utilizing β-actin as the internal control. This procedure normalizes the measurement of the mRNA target (Ct) and takes into consideration the alterations in the quantity of total RNA applied to each reaction (ΔCt). The relative Thy-1/MMP-9 amount differences were measured as fold alterations correspondent to the control in regards to the calibrator (ΔΔCt). Relative measurement of mRNA level was based on the formula of $2^{-\Delta\Delta Ct}$ as stated (Chao H M, Chen I L, Liu J H: S-allyl L-cysteine protects the retina against kainate excitotoxicity in the rat. *Am J Chin Med.* 2014, 42(3):693-708). The PCR reagents, software and machine were bought from AB Applied Biosystems. The results collected were compared for each management one by one, and a total percentage alteration correspondent to the control was measured. As outlined in Table 1, the following PCR oligonucleotide primers (β-actin, Thy-1 and MMP-9) were purchased at MISSION BIOTECH (Taipei, Taiwan).

TABLE 1

Sequences of Oligonucleotide Primers and Details of Polymerase Chain Reactions

| mRNA | Primers(5'→3') (F: Forward; R: Reverse) | Bases | Product Size (Base Pairs) | Cycles Profile (Denaturation/ Annealing/ Extension) (Temperature and Time in Seconds) | Cycles (Number) |
|---|---|---|---|---|---|
| β-Actin | F: AGGGAAATCGTGCGT GACAT (SEQ ID NO: 1) | 694-713 | 150 | 95°/95°/60° C. (20 s/3 s/30 s) | 40 |
| | R: GAACCGCTCATTGCC GATAG (SEQ ID NO: 2) | 824-843 | | | |
| Thy-1 | F: ACCAAGGATGAGGGC GACTA (SEQ ID NO: 3) | 380-399 | 120 | 95°/95°/60° C. (20 s/3 s/30 s) | 40 |
| | R: CAGGCTTATGCCACCA CATT (SEQ ID NO: 4) | 479-499 | | | |
| MMP-9 | F: TGCGCTGGGCTTAGAT CATT (SEQ ID NO: 5) | 1218-1237 | 105 | 95°/95°/60° C. (20 s/3 s/30 s) | 40 |
| | R: TGGATGCCTTTTATGTC GTCTTC (SEQ ID NO: 6) | 1300-1322 | | | |

Western Blotting Assay

One day following retinal ischemia with preadministration of relevant compounds or following a sham procedure, the animals were sacrificed. Retinal samples were retrieved and sonicated in a lysis buffer, mammalian protein extraction reagent (Pierce, Ill.). Equal amounts of denatured proteins (30 μg/20 μl/well) were processed on a sodium dodecyl sulfate polyacrylamide gel electrophoresis (SDS-PAGE; Bio-Rad, Hercules, Calif.) as described previously (Chao H M, Chuang M J, Liu J H, Liu X Q, Ho L K, Pan W H T, Zhang X M, Liu C M, Tsai S K, Kong C W, Lee S D, Chen M M, Chao F P: Baicalein protects against retinal ischemia by antioxidation, antiapoptosis, downregulation of HIF-1alpha, VEGF, and MMP-9 and upregulation of HO-1. *J Ocul Pharmacol Ther* 2013, 29:539-549). The nitrocellulose blots (NC) were next soaked 12 hours at 4° C. with various primary antibodies: mouse monoclonal [AC-15] anti-β-actin antibody (1:5,000; Abcam Inc., Cambridge, UK), rabbit monoclonal antibody Bcl-2 (50E3; 1:1000; Cell Signaling, Danvers, Mass. 01923, USA), mouse monoclonal antibody HO-1 (ab 13248) (1:1000; Abcam Inc., Cambridge, UK), mouse monoclonal antibody P-p38 MAPK (1:1000; Cell Signaling, Danvers, Mass. 01923, USA), rabbit monoclonal antibody p38 MAPK (1:1000; Cell Signaling, Danvers, Mass. 01923, USA) and rabbit monoclonal antibody MMP-9 (EP1255Y; 1:1000; Abcam Inc., Cambridge, UK). The blots were soaked with relevant secondary antibody, HRP-conjugated goat anti-rabbit or anti-mouse IgG (1:5,000 or 1:2,000; Amersham) at 37° C. for 1 h. Finally, the membranes were then developed, and exposed as described previously (Chao H M, Chuang M J, Liu J H, Liu X Q, Ho L K, Pan W H T, Zhang X M, Liu C M, Tsai S K, Kong C W, Lee S D, Chen M M, Chao F P: Baicalein protects against retinal ischemia by antioxidation, antiapoptosis, downregulation of HIF-1alpha, VEGF, and MMP-9 and upregulation of HO-1. *J Ocul Pharmacol Ther* 2013, 29:539-549), and then scanning densitometry was utilized to evaluate the level of each protein.

Gel Zymography

Protein samples were prepared in a similar manner to that described for the Western blotting analysis; these samples were then loaded onto and separated using 10% Tris-Glycine gel with 0.1% gelatin as protease substrate (Marecko I, Cvejic D, Selemetjev S, Paskas S, Tatic S, Paunovic I, Savin S: Enhanced activation of matrix metalloproteinase-9 correlates with the degree of papillary thyroid carcinoma infiltration. *Croat Med J* 2014, 55:128-137). After separation by electrophoresis, the gel was incubated in renaturation buffer (2.7% Triton X-100 in distilled water) at room temperature with gentle shaking for 30 minutes. The renaturation buffer was discarded and replaced with developing buffer (50 mmol/L Tris Base, 40 mmol/L HCl, 200 mmol/L NaCl, 5 mmol/L CaCl2, 0.2% Brij 35). After 30 minutes equilibration by the developing buffer, the gel was incubated with fresh developing buffer at 37° C. for 48 hours. After being developed, the gel was stained with 0.5% Coomassie Blue R-250 for 30 minutes and then destained appropriately. The visualized bands were then analyzed by scanning densitometry.

Statistical Analysis

Three or more groups were compared by one-way analysis of variance (ANOVA). The Tukey multiple-comparison test was further performed to compare the control column (for example, vehicle-treated ischemic retinas) to other columns (for example, CJDHW-treated ischemic retinas). A p value of <0.05 was defined as significant.

Results

The Effect of CJDHW on b-Wave

Figure 1B:
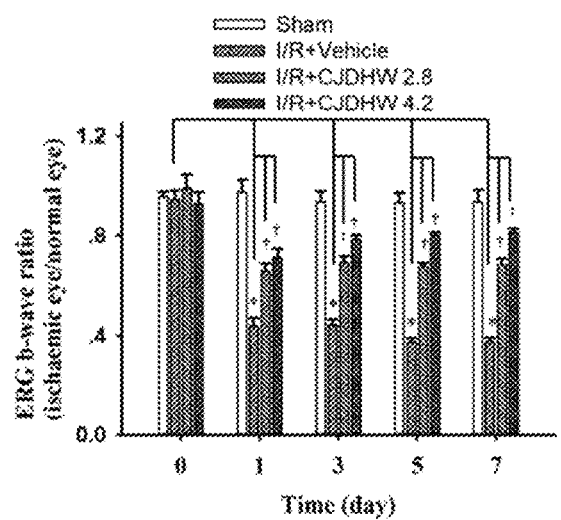
Figures 3A, 3B, 3C, 3D:
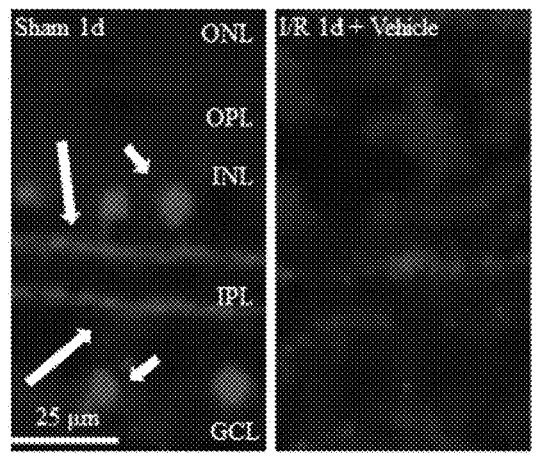
Figure 3E:
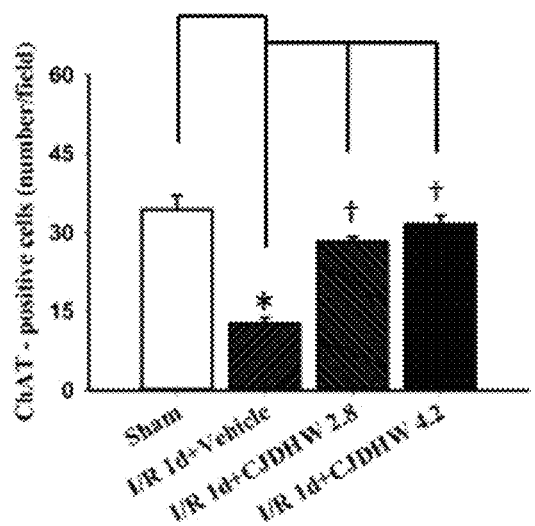
Figures 5F, 5G, 5H, 5I:
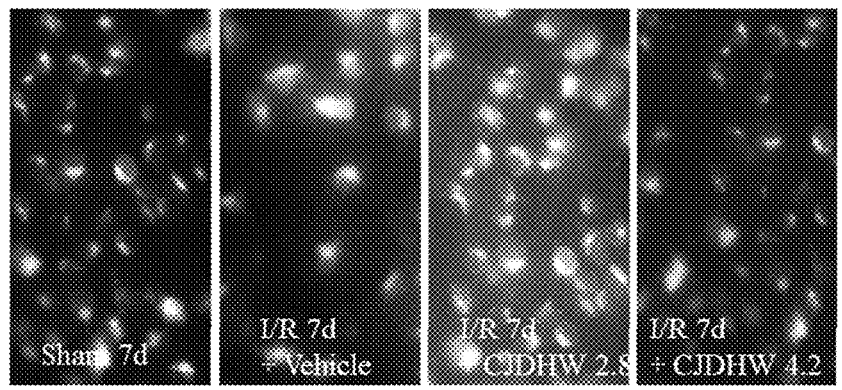
Figure 5J:
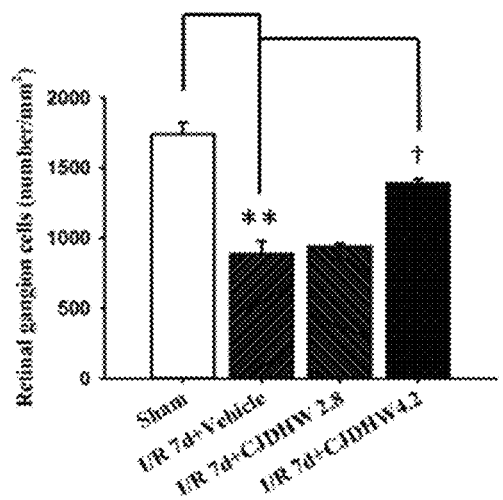

FIGS. 1A-1B showed the effect of CJDHW on retinal ischemia plus reperfusion (I/R) according to results from electroretinogram (ERG). In the sham retina (sham; FIG. 1A), the ERG b-wave was calculated at 0.98 mV. After retinal ischemia plus 1 day of reperfusion, the b-wave was considerably decreased. This decrease wasn't influenced with preadministration of vehicle (I/R+Vehicle: 0.11 mV; FIG. 1A). Nevertheless, preadministration of CJDHW (I/R+CJDHW 2.8 g/kg/day; I/R+CJDHW 4.2 g/kg/day) counteracted the ischemia-induced decrease in b-wave in a dose-responsive manner and the values increased to 0.26 and 0.39 mV, respectively, 1 day after I/R.

As shown in FIG. 1B (n=5), as compared with the preischemic b-wave ratio (baseline, day 0: 0.95±0.04), at 1, 3, 5, and 7 days after I/R with preadministration of vehicle (I/R+Vehicle), there exists a significant (p<0.05) b-wave ratio decrease (day 1: 0.44±0.03; day 3: 0.44±0.02; day 5: 0.37±0.02; day 7: 0.38±0.01). Nevertheless, after preadministration of CJDHW (I/R+CJDHW), there was a dose-responsive related (2.8 vs. 4.2 g/kg/day) and significant (p<0.05; at 2.8 and 4.2 g/kg/day) alleviation in the ischemia-induced b-wave ratio decrease on day 1 (0.66±0.03 vs. 0.72±0.03), day 3 (0.70±0.02 vs. 0.78±0.02), day 5 (0.68±0.02 vs. 0.80±0.01) and day 7 (0.69±0.02 vs. 0.81±0.01) after ischemia. Moreover, the preischemic b-wave ratio (day 0) was recorded at 0.99±0.05 versus 0.93±0.05.

On the other hand (figure not shown; n=5), when compared to the preischemic b-wave ratio (baseline at day 0: 1.04±0.04), 7 days after I/R and postischemic administration of vehicle, there is a significant (p<0.05) b-wave ratio reduction (0.34±0.08). In contrast, 7 days after I/R and postischemic administration of CJDHW, there was a concentration dependent (2.8 vs. 4.2 g/kg/day) and significant (p<0.05; at 4.2 g/kg/day) improvement in the ischemia-induced b-wave ratio reduction (0.56±0.07 vs. 0.61±0.07). nullifies the effect of ischemia/reperfusion (I/R 1 d+CJDHW4.2, 2D, 5E: 172.25±2.51 µm for whole retina, 38.99±1.85 for INL, 39.14±0.92 for IPL; I/R 7 d+CJDHW4.2, 2I, 5J: 171.78±5.19 µm for whole retina, 34.45±2.01 for INL, 33.53±0.92 for IPL). A quantitative analysis of the thickness of the various layers of the eye subjected to retinal ischemia and receiving different defined agents is shown in FIGS. 2E and 2J. At 7 days after ischemia, as compared to the sham group (76.48±0.70 µm), ischemia significantly reduced the thickness of the inner retinal layers (INL+IPL; 45.08±1.28 µm). This significant reduction was significantly attenuated in a dose-responsive manner by CJDHW (55.43±3.81 µm at 2.8 g/kg/day; 67.98±2.74 µm at 4.2 g/kg/day; picture not shown).

TABLE 2

Hematoxylin and Eosin Staining[§]

| Group | Sham | I/R + Vehicle | I/R + CJDHW2.8 | I/R + CJDHW4.2 |
|---|---|---|---|---|
| Retinal thickness at day 1 | | | | |
| Whole | 174.01 ± 1.66 | 162.42 ± 2.98** | 165.95 ± 4.40 | 172.25 ± 2.51[†] |
| INL | 40.08 ± 1.43 | 33.13 ± 1.44* | 36.77 ± 1.58 | 38.99 ± 1.85[†] |
| IPL | 41.29 ± 1.01 | 36.06 ± 0.76** | 37.16 ± 2.28 | 39.14 ± 0.92[†] |
| Retinal thickness at day 7 | | | | |
| Whole | 180.25 ± 1.77 | 141.02 ± 4.24** | 156.18 ± 3.96[†] | 171.78 ± 5.19[††] |
| INL | 38.1 ± 0.57 | 24.74 ± 1.61** | 29.23 ± 2.71 | 34.45 ± 2.01[†] |
| IPL | 38.38 ± 0.58 | 20.34 ± 0.80** | 26.20 ± 1.80[†] | 33.53 ± 0.92[††] |

[§]In comparison of the control retina, 1 or 7 days following sham procedure (Sham 1 day, n = 8; Sham 7 day, n = 6), after retinal ischemia plus 1 or 7 days of reperfusion and pretreatment with vehicle (I/R 1 day + Vehicle, n = 4; I/R 7 day + Vehicle, n = 5), there was a significant decrease (*p < 0.05; **p < 0.01) in the thickness of the whole retina, the INL and the IPL. In contrast, this significant decrease was dose-dependently (with a less effect at 2.8 g/Kg/day, I/R + CJDHW2.8, n = 4) and significantly ([†]p < 0.05; [††]p < 0.01; I/R + CJDHW2.8; I/R + CJDHW4.2, n = 4) inhibited by pretreatment with CJDHW. The results were the mean ± SEM (µm).
Abbreviations:
CJDHW4.2, Chi-Ju-Di-Huang-Wan at 4.2 g/Kg/day;
INL, inner nuclear layer;
IPL, inner plexiform layer.

When the ERG b-wave ratios were compared (sham eye vs. fellow normal eye), no significant difference existed between the pre-sham ERG b-wave ratio (day 0) and post-sham one (day 1, 3, 5, or 7).

CJDHW's Influence on the Thickness of the Various Retinal Layers Stained by HE

FIGS. 2A-2J and Table 2 show retinal sections from similar eccentricity (1 mm from disc) of four groups (n=4~6) where it can be seen that when compared with the sham procedure retina (Sham 1 d, 2A, 2E: 174.0±1.66 µm for whole retina, 40.08±1.43 µm for INL, 41.29±1.01 µm for IPL; Sham 7 d, 2F, 2J: 180.25±1.77 µm for whole retina, 38.10±0.57 µm for INL, 38.38±0.58 for IPL), following ischemia plus 1 and 7 days of reperfusion with preadministration of vehicle [I/R 1 d+Vehicle (2B, 2E) vs. I/R 7 d+Vehicle (2G, 2J)], the INL (33.13±1.44 vs. 24.74±1.61 µm), the IPL (36.06±0.76 vs. 20.34±0.80 µm), and the whole retina (162.42±2.98 vs. 141.02±4.24 µm) were significantly (*p<0.05; **p<0.01) reduced in the thickness. Treatment of animals with CJDHW dose-dependently (with a less effect at 2.8 g/kg/day; I/R 1 d+CJDHW2.8, 2C, 2E: 165.95±4.40 µm for the whole retina, 37.52±1.05 for the INL, 37.16±2.28 for the IPL; I/R 7 d+CJDHW2.8, 2H, 2J: 156.18±3.96 µm for the whole retina, 29.23±2.71 for the INL, 26.20±1.80 for the IPL) and significantly († p<0.05; †† p<0.01; at 4.2 g/kg/day)

The Influence of CJDHW on ChAT Immunolabeling

In FIGS. 3A-3J and Table 3 (n=6), at 1 and 7 days after the sham procedure (control: 3A and 3E; 3F and 3J), ChAT (red) immunolabeling was related to the amacrine cell bodies (short arrows; Sham 1 d, 3A, 3E: 34.33±2.70 cells/field; Sham 7 d, 3F, 3J: 36.83±2.73 cells/field) in the inner nuclear layer (INL) and the ganglion cell layer (GCL); moreover, their neuronal processes existed as 2-strata picture in the inner plexiform layer (IPL; long arrows), as has been described elsewhere (Chao H M, Chen I L, Liu J H: S-allyl L-cysteine protects the retina against kainate excitotoxicity in the rat. Am J Chin Med. 2014, 42(3):693-708). In the ischemic retina that had undergone preadministration of vehicle, the amacrine cell body immunolabeling (I/R 1 d+Vehicle, 3B, 3E: 12.67±1.15 cells/field; I/R 7 d+Vehicle, 3G, 3J: 13.17±1.66 cells/field) was almost absent following retinal ischemia plus 1 and 7 days of reperfusion; moreover, the IPL immunoreactivity was drastically decreased. Most importantly, the effect of I/R underwent a significant attenuation in a dose-responsive manner when there had been preadministration of low (I/R 1 d+CJDHW 2.8 g/kg/day, 3C, 3E: 28.33±0.88 cells/field; I/R 7 d+CJDHW 2.8 g/kg/day, 3H, 3J: 23.50±1.41 cells/field) or high dose of CJDHW (I/R 1 d+CJDHW 4.2 g/kg/day, 3D, 3E: 31.67±1.59 cells/field; I/R 7 d+CJDHW 4.2 g/kg/day, 3I, 3J: 28.50±1.88 cells/field).

TABLE 3

Choline acetyltransferase (ChAT) immunolabelling[§]

| Group | Sham | I/R + Vehicle | I/R + CJDHW2.8 | I/R + CJDHW4.2 |
|---|---|---|---|---|
| Cholinergic amacrines (number/field) at day 1 | 34.33 ± 2.69 | 12.67 ± 1.15* | 28.33 ± 0.88[†] | 31.67 ± 1.59[†] |
| Cholinergic amacrines (number/field) at day 7 | 36.83 ± 2.73 | 13.17 ± 1.66* | 23.50 ± 1.41[†] | 28.50 ± 1.88[†] |

[§]In comparison of the control retina, 1 or 7 days following sham procedure (Sham), after retinal ischemia plus 1 or 7 days of reperfusion and pretreatment with vehicle (I/R + Vehicle), the number of CHAT-immunolabeling amacrine cells per field was significantly decreased (*p < 0.05) in the inner nuclear layer and the ganglion cell layer. In contrast, this significant decrease was dose-dependently (with a less effect at 2.8 g/Kg/day, I/R + CJDHW2.8) and significantly ([†]p < 0.05; I/R + CJDHW2.8; I/R + CJDHW4.2) inhibited by pretreatment with CJDHW. The results were the mean ± SEM (μm; n = 6).
Abbreviations:
CJDHW4.2, Chi-Ju-Di-Huang-Wan at 4.2 g/Kg/day;
INL, inner nuclear layer;
IPL, inner plexiform layer.

The Effect of CJDHW on Vimentin or GFAP Immunoreactivity

In FIGS. 4A-4R, 1 and 7 days after the sham procedure (control; Sham 1 d, 4B; Sham 7 d, 4K), the vimentin immunolabeling of Müller cell processes extended from the end foot to the IPL as well as into the INL and the outer nuclear layer (ONL), as has been described elsewhere (Chao H M, Chen I L, Liu J H: S-allyl L-cysteine protects the retina against kainate excitotoxicity in the rat. Am J Chin Med. 2014, 42(3):693-708). Anti-vimentin immunolabeling was enhanced 1 and 7 days after I/R with preadministration of vehicle (I/R 1 d+Vehicle, 4C; I/R 7 d+Vehicle, 4L). Nevertheless, the ischemic effect was alleviated by preadministration of low (I/R 1 d+CJDHW 2.8 g/kg/day, 4D; I/R 7 d+CJDHW 2.8 g/kg/day, 4M) or high dose of CJDHW (I/R 1 d+CJDHW 4.2 g/kg/day, 4E; I/R 7 d+CJDHW 4.2 g/kg/day, 4N). DAPI (blue; 4A; 4J) was utilized to immunolabel the cellular nuclei in the normal control.

When compared with the control retina (Sham 1 d, 4F; Sham 7 d, 4O), anti-GFAP immunoreactivity was also enhanced 1 and 7 days after retinal ischemia when there had been preadministration of vehicle (I/R 1 d+Vehicle, 4G; I/R 7 d+Vehicle, 4P). This enhancement was nullified by preadministration of a low (I/R 1 d+CJDHW 2.8 g/kg/day, 4H; I/R 7 d+CJDHW 2.8 g/kg/day, 4Q) or a high dose of CJDHW (I/R 1 d+CJDHW 4.2 g/kg/day, 4I; I/R 7 d+CJDHW 4.2 g/kg/day, 4R).

The Effect of CJDHW on the Presence of Apoptotic Cells in the RGC Layer

In Table 4 (n=5), in contrast with the control retina at 1 or 7 days after sham procedure (Sham at days 1 and 7: no TUNEL-positive cells), at 1 or 7 days after ischemia and preadministration with vehicle, there were significantly (**p<0.01) more numerous (I/R+Vehicle at day 1: 1.40±0.25 cells/field; at day 7: 1.4±0.24 cells/field) TUNEL-positive cells in the RGC layer. This increase was alleviated in a dose-responsive manner (with a less effect at 2.8 g/kg/day; I/R+CJDHW2.8 at day 1: 0.80±0.20 cells/field; at day 7: 0.80±0.37 cells/field) and significantly ([†]p<0.05; at 4.2 g/kg/day) at 1 or 7 days after ischemia when there had been preadministration of CJDHW (I/R+CJDHW4.2 at day 1: 0.40±0.25 cells/field; at day 7: 0.60±0.24 cells/field).

TABLE 4

Terminal Deoxynucleotidyl-Transferase dUTP Nick End-Labeling (TUNEL)

| Group | Sham | I/R + Vehicle | I/R + CJDHW2.8 | I/R + CJDHW4.2 |
|---|---|---|---|---|
| Apoptotic cell No. at day 1 | 0 | 1.40 ± 0.25** | 0.80 ± 0.20 | 0.40 ± 0.25[†] |
| Apoptotic cell No. at day 7 | 0 | 1.40 ± 0.24** | 0.80 ± 0.37 | 0.60 ± 0.24[†] |

Retrograde Fluorogold Immunolabeling of RGCs

In FIG. 5 and Table 5 (n=3), 1 and 7 days following the sham procedure, the density of RGCs was 1952.16±72.33 (Sham 1 d) and 1737.23±87.72 cells/mm$^2$ (Sham 7 d). As a comparison, 1 and 7 days following retinal ischemia after preadministration of vehicle, the RGC density was significantly decreased to 929.01±77.94 (I/R 1 d+Vehicle) and 887.73±91.32 (I/R 7 d+Vehicle). This decrease was alleviated in a dose-responsive manner (with a less effect at 2.8 g/kg/day; I/R 1 d+CJDHW2.8: 1112.65±94.74 cells/mm$^2$; I/R 7 d+CJDHW2.8: 941.89±22.47). This alleviation was significant when there had been preadministration of high dose of CJDHW (I/R 1 d+CJDHW4.2 g/kg/day: 1691.36±137.16; I/R 7 d+CJDHW4.2 g/kg/day: 1389.02±30.72).

TABLE 5

Fluorogold-immunolabeling

| Group | Sham | I/R + Vehicle | I/R + CJDHW2.8 | I/R + CJDHW4.2 |
|---|---|---|---|---|
| RGCs (number/mm$^2$) at day 1 | 1952.16 ± 72.33 | 929.01 ± 77.94** | 1112.65 ± 94.74 | 1691.36 ± 137.16[†] |
| RGCs (number/mm$^2$) at day 7 | 1737.23 ± 87.72 | 887.73 ± 91.32** | 941.89 ± 22.47 | 1389.02 ± 30.72[†] |

CJDHW's Influence on the Retinal mRNA Concentrations of Thy-1, MMP-9

Figure 6:
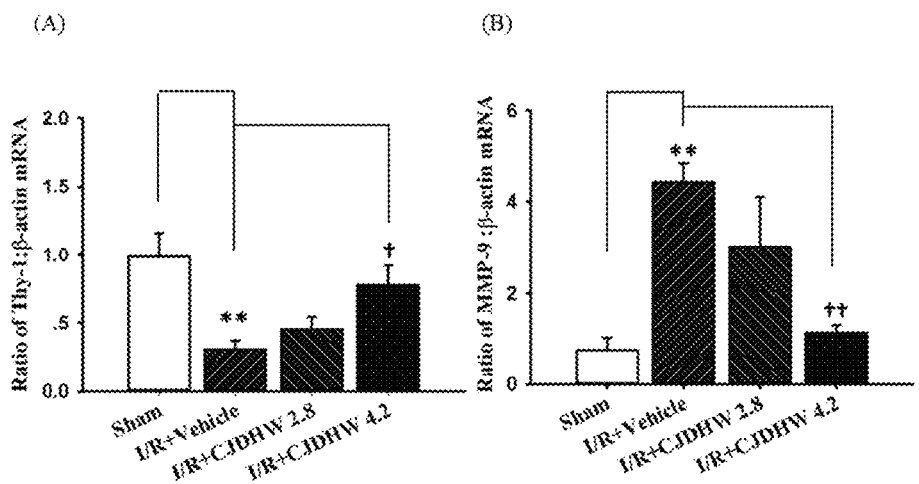
FIG. 6: The mRNA expression levels of Thy-1 (A), MMP-9 (B) and β-actin. In retinal ischemia plus 24 h of reperfusion (I/R), total mRNA was extracted and isolated from the sham procedure retinas (Sham) or the ischemic retinas administered with vehicle (water), or low (2.8 g/kg/day)/high dose (4.2 g/kg/day) of CJDHW. The effect of each defined compound on the mRNA concentrations of Thy-1/MMP-9 divided by the mRNA levels of β-actin was evaluated. ** represents significance ($p<0.01$; sham vs. I/R+Vehicle). † or †† represents significance for Thy-1 ($p<0.05$; I/R+Vehicle vs. I/R+CJDHW4.2) or significance for MMP-9 ($p<0.01$; I/R+Vehicle vs. I/R+CJDHW4.2), respectively. Abbreviations: CJDHW, Chi-Ju-Di-Huang-Wan; MMP-9, matrix metalloproteinase-9. The findings are presented as the mean±SEM (Thy-1, n=5; MMP-9, n=3~4).
Figure 7:
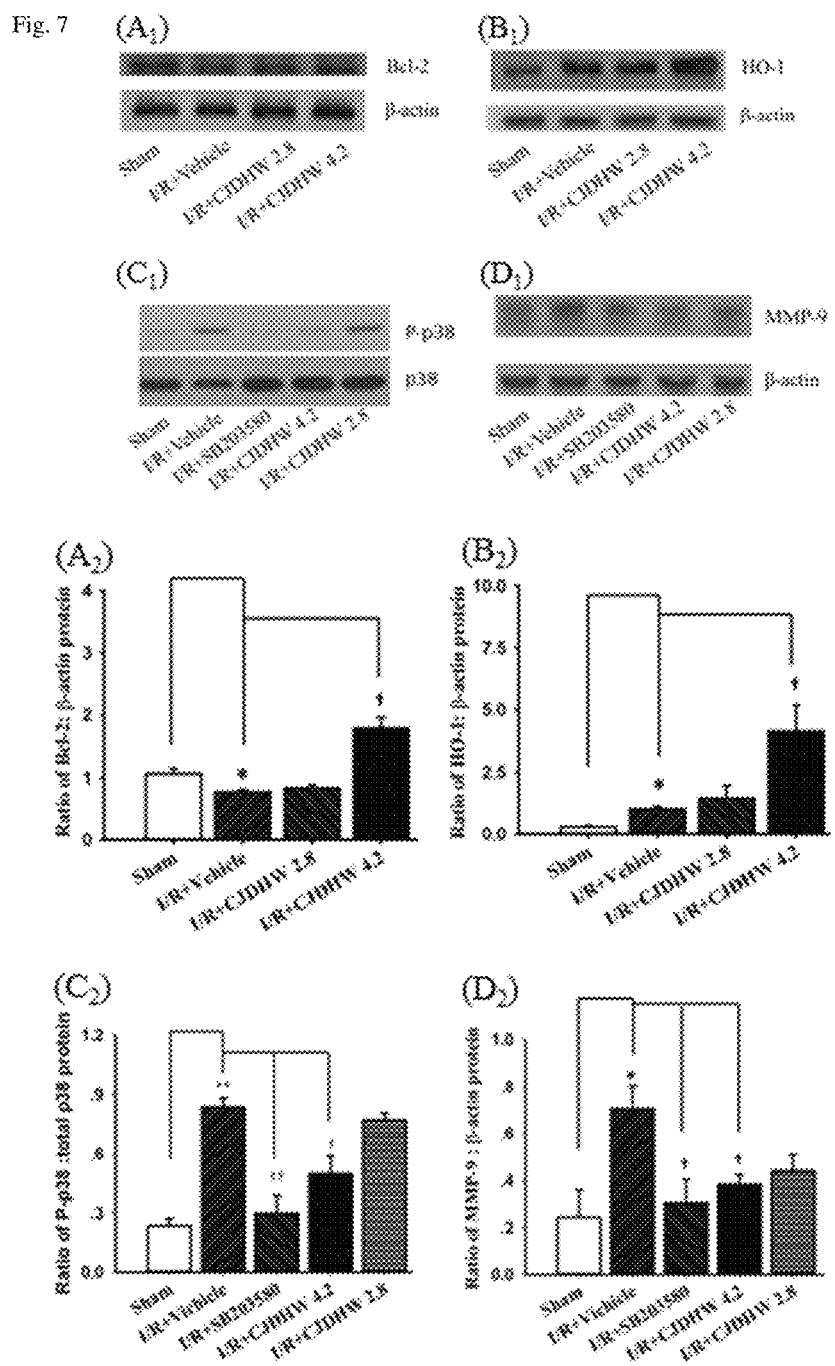
FIG. 7: Western blotting. The antibodies against Bcl-2 (A1), HO-1 (B1), P-p38 (C1), MMP-9 (D1) and β-actin are respectively shown as 26-kDa, 34.6-kDa, 43-kDa, 92~96-kDa and 43-kDa bands. Each bar represents the ratio of Bcl-2 (n=4~9; A2), HO-1 (n=4; B2), P-p38 (n=5~9; C2), or MMP-9 (n=5; D2) to β-actin. * or † represents significance ($p<0.05$; sham vs. I/R+Vehicle) or significance ($p<0.05$; I/R+Vehicle vs. I/R+CJDHW4.2; I/R+Vehicle vs. SB203580), respectively. Additionally, for P-p38, ** or ††/† represents significance ($p<0.01$; sham vs. I/R+Vehicle) or significance ($p<0.01/p<0.05$; I/R+Vehicle vs. SB203580/I/R+Vehicle vs. I/R+CJDHW4.2), respectively. Abbreviations: CJDHW, Chi-Ju-Di-Huang-Wan; HO-1, heme oxygenase-1; P-p38, phosphorylated-p38. The results are mean±SEM.

As shown in FIG. 6 and Table 6 (n=5 for Thy-1; n=3~4 for MMP-9), in contrast with the control sham retina, the ratios for Thy-1 and MMP-9 in the vehicle-pretreated ischemic retina were significantly (**$p<0.01$) altered 24 hours following retinal ischemia. As compared to the vehicle-preadministered ischemic retina, the ischemic retina that had undergone preadministration of CJDHW showed a dose-response related (with a less effect at 2.8 g/kg/day) and significant ($p<0.05$; at 4.2 g/kg/day) nullification of the overexpression of MMP-9 together with a significant ($p<0.05$; at 4.2 g/kg/day) blunting of underexpression of Thy-1.

TABLE 6

The ratios of mRNA concentration of Thy-1 or MMP-9 to that of β-actin

| Group | Sham | I/R + Vehicle | I/R + CJDHW2.8 | I/R + CJDHW4.2 |
|---|---|---|---|---|
| Thy-1/β-actin (n = 5) | 0.99 ± 0.17 | 0.31 ± 0.07** | 0.45 ± 0.09 | 0.78 ± 0.14† |
| MMP-9/β-actin (n = 3~4) | 0.75 ± 0.27 | 4.44 ± 0.42** | 3.01 ± 1.09 | 1.13 ± 0.17† |

The Effect of CJDHW on the Protein Expression Levels of In Vivo Retinal Proteins, Namely Bcl-2, HO-1, P-p38 MAPK and MMP-9 Relative to the Protein Expression Level of β-Actin As shown in FIG. 7 and Table 7 (n=4~9 for Bcl-2; n=4 for HO-1; n=5~9 for P-p38; n=5 for MMP-9), in contrast with the control sham retina, 24 hours following sham procedure (Sham), after retinal ischemia plus 24 hours of reperfusion and pretreatment with vehicle there was a significant decrease (*$p<0.05$) in the ratios for Bcl-2 or increase (*$p<0.05$ or **$p<0.01$) in the ratios for HO-1, P-p38 and MMP-9. In contrast, these significant changes underwent dose-responsive (with a less effect of CJDHW2.8) and significant alterations (†$p<0.05$ for I/R+CJDHW2.8 or I/R+CJDHW4.2; †$p<0.05$ or ††$p<0.01$ for I/R+SB203580) after pretreatment with CJDHW and/or SB203580 (p38 MAPK inhibitor), as well as a further significant (†$p<0.05$ for I/R+CJDHW4.2) increase in the protein expression of HO-1. Notwithstanding the above changes, the total p38 protein levels in the retina were unchanged across the various defined groups (data not shown).

TABLE 7

Western blotting. The ratios of protein concentration of Bcl-2, HO-1, P-p38 or MMP-9 to that of β-actin

| Group | Sham | I/R + Vehicle | I/R + SB203580 | I/R + CJDHW2.8 | I/R + CJDHW4.2 |
|---|---|---|---|---|---|
| Bcl-2/β-actin (n = 4~9) | 1.06 ± 0.08 | 0.78 ± 0.04* | Not available | 0.83 ± 0.06 | 1.80 ± 0.17† |
| HO-1/β-actin (n = 4) | 0.27 ± 0.06 | 0.99 ± 0.10* | Not available | 1.46 ± 0.49 | 4.15 ± 1.04† |
| P-p38/β-actin (n = 5~10) | 0.17 ± 0.02 | 1.02 ± 0.11** | 0.23 ± 0.05†† | 0.76 ± 0.09† | 0.60 ± 0.06† |
| MMP-9/β-actin (n = 5) | 0.25 ± 0.12 | 0.70 ± 0.10* | 0.31 ± 0.10† | 0.44 ± 0.07 | 0.39 ± 0.04† |

When MMP-9 activity in the retina was detected by zymography (FIG. 8; Table 8; n=4~5), in contrast with the sham procedure control retina (Sham), 24 hours following sham procedure (Sham), the MMP-9 activity (I/R+Vehicle) in the vehicle (DMSO)-pretreated ischemic retina was significantly (**$p<0.01$) enhanced 24 hours following ischemia. However, compared to the vehicle-pretreated ischemic retina, the ischemic retina preadministered with CJDHW or SB203580 (p38 MAPK inhibitor) demonstrated a dose-response related (with a less effect at 2.8 g/kg/day of CJDHW) and significant (††$p<0.01$; for I/R+CJDHW4.2 and I/R+SB203580) alleviation of the increase in MMP-9 activity.

TABLE 8

Gel zymography. The ratios of protein concentration of MMP-9 to that of β-actin

| Group (n = 4~5) | Sham | I/R + Vehicle | I/R + SB203580 | I/R + CJDHW2.8 | I/R + CJDHW4.2 |
|---|---|---|---|---|---|
| MMP-9/β-actin | 1.0 ± 0.0 | 5.03 ± 0.70** | 1.49 ± 0.21†† | 3.05 ± 0.44 | 1.59 ± 0.21†† |

One skilled in the art readily appreciates that the present invention is well adapted to carry out the objects and obtain the ends and advantages mentioned, as well as those inherent therein. The methods and uses thereof are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for treating retinal ischemia, or a disease, condition, or disorder associated with retinal ischemia, in a subject in need thereof, comprising administering to said subject a therapeutically effective amount of Chi-Ju-Di-Huang-Wan, wherein the Chi-Ju-Di-Huang-Wan consists of Rehmanniae Radix Preparata, Corni Fructus, Rhizoma *Dioscoreae*, Poria, Cortex Moutan Radicis, Alismatis Rhizome, Fructus Lycii, and *Chrysanthemi* Flos.

2. The method of claim 1, wherein the method further comprises administering to said subject honey.

3. The method of claim 1, wherein the disease, condition, or disorder associated with retinal ischemia comprises retinal vascular occlusion, glaucoma, diabetic retinopathy, or age related macular degeneration.

4. The method of claim 1, wherein the subject is a mammal.

5. The method of claim 4, wherein the subject is a human.

6. The method of claim 4, wherein the dose of Chi-Ju-Di-Huang-Wan for human ranges from 0.1 g/kg/day to 2 g/kg/day.

7. The method of claim 5, wherein the dose of Chi-Ju-Di-Huang-Wan for human ranges from 0.4 g/kg/day to 0.7 g/kg/day.

8. The method of claim 1, wherein the composition is administered orally.

* * * * *